(12) United States Patent
Iwasaki et al.

(10) Patent No.: US 8,916,389 B2
(45) Date of Patent: Dec. 23, 2014

(54) SENSOR ELEMENT FOR SPR MEASUREMENT

(75) Inventors: Yuzuru Iwasaki, Atsugi (JP); Michiko Seyama, Atsugi (JP); Toru Miura, Atsugi (JP); Tsutomu Horiuchi, Atsugi (JP); Tsuneyuki Haga, Atsugi (JP); Serge Camou, Atsugi (JP)

(73) Assignee: Nippon Telegraph and Telephone Corporation, Tokyo (JP)

( * ) Notice: Subject to any disclaimer, the term of this patent is extended or adjusted under 35 U.S.C. 154(b) by 1637 days.

(21) Appl. No.: 12/303,693

(22) PCT Filed: Jun. 26, 2007

(86) PCT No.: PCT/JP2007/062758
§ 371 (c)(1),
(2), (4) Date: Apr. 14, 2010

(87) PCT Pub. No.: WO2008/001748
PCT Pub. Date: Jan. 3, 2008

(65) Prior Publication Data
US 2010/0233028 A1    Sep. 16, 2010

(30) Foreign Application Priority Data

Jun. 26, 2006   (JP) ................................. 2006-175684

(51) Int. Cl.
*G01N 33/553* (2006.01)
*G01N 33/53* (2006.01)
(Continued)

(52) U.S. Cl.
CPC ............ *G01N 21/553* (2013.01); *G01N 33/553* (2013.01); *G01N 33/543* (2013.01);
(Continued)

(58) Field of Classification Search
None
See application file for complete search history.

(56) References Cited

U.S. PATENT DOCUMENTS

| 5,955,729 | A | 9/1999 | Nelson et al. |
| 2003/0013206 | A1* | 1/2003 | Takahashi et al. ............ 436/514 |
| 2003/0017579 | A1 | 1/2003 | Corn et al. |

FOREIGN PATENT DOCUMENTS

| EP | 0343826 A1 | 11/1989 |
| EP | 0869351 A2 | 10/1998 |

(Continued)

OTHER PUBLICATIONS

Joo-Eun Kim et al., *Functional Membrane-Implanted Lab-on-a-Chip for Analysis of Percent HDL Cholesterol*, Analytical Chemistry, vol. 77, 2005, pp. 7901-7907.

(Continued)

*Primary Examiner* — Neil N Turk
(74) *Attorney, Agent, or Firm* — Workman Nydegger (57) ABSTRACT

An object of the present invention is to provide an element for SPR measurement without the need of a mechanical solution-sending mechanism. The scope of the present invention is defined by a sensor element for surface plasmon resonance (SPR) measurement utilizing an SPR effect, wherein the sensor element comprises a transparent substrate, a gold thin film formed on at least a part of the transparent substrate, and a thin film with affinity for a sample provided on the transparent substrate having the gold thin film formed on at least a part thereof, and the thin film with affinity for a sample has a measurement region (region A), a sample introduction section (region B) and a sample absorption section (region C) provided with the region A therebetween, the region A is provided with a sample measurement section containing a molecule-recognizing film, an introduction port is formed on the film with affinity for a sample in the region B, an absorption pad is provided on the film with affinity for a sample in the region C so that the whole region C should be covered, and a point in the region B, a point in the region A, and a point in the region C exist in one straight line on the thin film with affinity for a sample.

16 Claims, 5 Drawing Sheets

(51) Int. Cl.
    *G01N 33/52* (2006.01)
    *G01N 21/55* (2014.01)
    *G01N 33/543* (2006.01)
    *G01N 33/544* (2006.01)

(52) U.S. Cl.
    CPC .......... *G01N 33/53* (2013.01); *G01N 33/54373* (2013.01)
    USPC ........... 436/518; 436/180; 436/525; 436/530; 436/535; 422/50; 422/82.05; 422/400; 422/401; 422/411; 435/6.1; 435/7.1

(56) References Cited

FOREIGN PATENT DOCUMENTS

| | | |
|---|---|---|
| EP | 2028475 A1 | 2/2009 |
| JP | 07-036017 | 2/1995 |
| JP | 7-36017 | 4/1995 |
| JP | 11-037922 | 2/1999 |
| JP | 11512518 | 10/1999 |
| JP | 2000-097944 | 4/2000 |
| JP | 2002-014097 | 1/2002 |
| JP | 3294605 | 4/2002 |
| JP | 2004-526973 | 9/2004 |
| WO | WO 02/086513 A2 | 10/2002 |

OTHER PUBLICATIONS

OR Tanaka, et al., *Study of High-Sensitive Analysis Using Immunochromato Test Strip Sensor*, Denki Kagaku Shuki Taikai Koen Yoshishu, 2005 Nen, p. 25 (English translation included).

Supplementary European Search Report dated May 19, 2009 from related European Patent Application No. 07767564.3 (6 pages).

PCT Notification of Transmittal of Translation of the International Preliminary Report on Patentability (Chapter I or Chapter II of the Patent Cooperation Treaty) of related Japanese Application No. PCT/JP2007/062758, dated Feb. 12, 2009 (8 pages).

Summons to attend oral proceedings issued on Dec. 22, 2010 in corresponding European Patent Application No. 07767564.3.

Emanuel et al., "Recombinant antibodies: a new reagent for biological agent detection," Biosensors & Bioelectronics 14 (2000), pp. 751-759.

Official Notice of Rejection from related Japanese Application No. 547259 dated Aug. 12, 2011.

\* cited by examiner

DROPPED SAMPLE

FIG.3A

CUP

FIG.3B

PAD

FILM WITH AFFINITY FOR SAMPLE

FIG.5A

PORTION ON WHICH ANTIBODY IS IMMOBILIZED

FIG.5B

SENSOR ELEMENT FOR SPR MEASUREMENT

TECHNICAL FIELD

The present invention relates to a sensor element for surface plasmon resonance (SPR) measurement. This sensor is used in a sensor for biochemical diagnoses in humans and animals, environmental analyses, measurement of biomolecular interaction for biochemical researches, and the like. More specifically, the present invention is used in an immunosensor for quantifying an antigen or an antibody, a sensor for identifying a DNA sequence, a sensor for quantifying a substrate of an enzyme, a sensor for identifying a pathogen, or the like.

BACKGROUND ART

As one of methods for measuring a chemical substance in a liquid sample, methods using a molecule-recognizing material are known. As one of the methods using the molecule-recognizing material, an immunosensor utilizing an antigen-antibody reaction is used.

Since an antibody has a strong molecule recognizing characteristic, and techniques for preparing an antibody specifically binding to a component to be measured have been developed, an immunosensor using an antibody has been increasingly used for detection of a virus or for measurement or rapid diagnosis of a disease marker or an environmental pollutant.

For example, in a sandwich-type enzyme-linked immunosorbent assay (ELISA) commonly used as an immunoassay, a plurality of kinds of antibodies that bind to different sites in one antigen need to be prepared, and a labeling molecule needs to be bound to one of these antibodies.

Furthermore, in this sandwich-type ELISA, 1) antibodies specifically binding to a target antigen are prepared on a solid phase; 2) a solution containing a target substance is added to this solid phase, and the antigen is allowed to bind to the solid phase by an antigen-antibody reaction; 3) excess proteins and antigens that have not bound to the solid phase are removed by washing; 4) then a labeled antibody is added to solid phase and allowed to bind to the antigen; 5) and the antigen is quantified using the immobilized labeled antibody.

Therefore, to perform an analysis with this operating procedure, pipetting, washing, and exchanging a liquid are required, and an absorption spectrometer or a fluorescence spectrometer is required for the final measurement. Therefore, ELISA suffers from problems such as a high testing cost and a complex procedure.

Meanwhile, in the field of immunoassay, an immunological chromatographic method has been developed as a simple and inexpensive method (for example, refer to Patent Document 1).

The immunological chromatographic method is a measurement method for detecting the presence of an antigen with the following mechanism of action. 1) A sample such as urine, blood, or a mucous membrane suspension containing an antigen to be measured is added dropwise onto a sample drop section of a filter paper containing a gold colloid-labeled antibody at a predetermined position and developed. 2) When the sample containing the antigen is developed, the antigen is brought into contact with the gold colloid-labeled antibody, and the gold colloid-labeled antibody binds to the antigen by an antigen-antibody reaction. 3) When the gold colloid-labeled antibody bound to the antigen is developed, the antibody binds to a second antibody immobilized beforehand at a predetermined position of the filter paper, and gold colloid is accumulated in this portion. 4) Accumulation of gold colloid results in purple-red coloration. The presence of the antigen is detected by accumulation of gold colloid.

Since chromatography using a filter paper is utilized in this method, there is a separation action of separating the measurement object and impurities, and even a sample containing many impurities can be measured. Furthermore, since no special device is required, and a result can be visually determined, the method is used in testing for influenza virus, pregnancy test, and the like as a simple method for measuring an antigen.

Furthermore, in the cases where measurement of a trace amount is required, for example, introduction of a label into an antibody causes a loss of the antibody activity or a change in recognition of an antigen, a small amount of the antibody is obtained, or the like, a special measurement method is required.

As one of such measurement methods, a measurement chip is used in which a filter paper is placed in a plastic passage (for example, refer to Non-patent Document 1). In this measurement chip, a component to be measured is separated from impurities by development in the planar surface of the filter paper and then led to a clear chamber, and the component to be measured is quantified by intensity of a light transmitted through the chamber.

One of methods of measuring a biomolecular interaction such as an antigen-antibody reaction using an unlabeled antibody or antigen or DNA hybridization is an SPR measurement method utilizing effects of a surface plasmon resonance, and an SPR sensor is used in this measurement method.

The SPR sensor is an immunosensor utilizing an antigen-antibody reaction, which comprises a metal thin film on which an antigen or an antibody is immobilized. The antigen or the antibody immobilized on the metal thin film binds to an antibody or an antigen by an antigen-antibody reaction. When the antigen or the antibody binds to an antibody or an antigen by an antigen-antibody reaction, a change occurs in a refractive index. The antibody or the antigen is detected by detecting the change in the refractive index. Since it is unnecessary to label a molecule to be detected with a radioactive substance or a fluorescent substance, and high concentration sensitivity can be obtained, the SPR sensor has been increasingly used as means for detecting a biologically-relevant substance (for example, refer to Patent Document 2).

The SPR measurement is characterized in that only a small volume of a sample required is necessary for measurement since a refractive index is measured in a range of a volume that an evanescent light reaches in a portion on the gold thin film on which a light is reflected. Furthermore, in the SPR measurement, an optical system for measuring an SPR phenomenon and a measurement element for performing an antigen-antibody reaction can be separated using a transparent substrate, and replacement of the measurement element enables measurement of a different molecule sample as well as prevention of contamination of the measurement device. In particular, when a sample contains a toxin, leakage of the toxin can be prevented. Furthermore, a plurality of samples can be measured at the same time in the SPR measurement, resulting in a high measurement throughput.

Patent Document 1: Japanese Patent Publication No. H07-36017 (1995)
Patent Document 2: Japanese Patent No. 3294605
Non-patent Document 1: Anal. Chem. 2005, 77, 7901-7907

DISCLOSURE OF THE INVENTION

In an immunological chromatographic method, antibodies need to be prepared so that two antibodies can bind to one antigen at the same time. In addition, gold colloid needs to be bound to one of these antibodies so that an activity thereof should not be decreased. Thus, preparation of antibodies requires costs and time.

Meanwhile, in conventional SPR measurement, it is necessary to use only one kind of antibody, and sensitivity is high, but a passage structure and a solution-sending device for sending a sample solution to the passage structure are required. Furthermore, a region in which a refractive index can be measured by SPR is very narrow. When a solution is sent only to this region using an existing solution-sending device, a very high pressure is required to send a solution. Therefore, SPR measurement has a problem that a volume more than essentially necessary for measurement is required, and it is difficult to increase the absolute amount sensitivity (sensitivity per required sample amount).

To achieve a good balance of simple measurement and high sensitivity measurement, an object of the present invention is to provide an element for SPR measurement that does not require a mechanical solution-sending mechanism.

Specifically, the sensor element for SPR measurement of the present invention is characterized in that the sensor element comprises a transparent substrate, a gold thin film formed on at least a part of the transparent substrate, and a thin film with affinity for a sample provided on the transparent substrate having the gold thin film formed on at least a part thereof, and the transparent substrate having the gold thin film and the thin film with affinity for a sample provided thereon has a measurement region (region A), a sample introduction section (region B) and a sample absorption section (region C) provided with the region A therebetween, the thin film with affinity for a sample is provided on at least a part of the surface in all the regions A, B, and C, the thin film with affinity for a sample in the region A is provided with a sample measurement section containing a molecule-recognizing film, an introduction port is formed on the film with affinity for a sample in the region B, an absorption pad is provided on the film with affinity for a sample in the region C so that the whole region C should be covered, and a point in the region B, a point in the region A, and a point in the region C exist in one straight line on the thin film with affinity for a sample. The gold thin film may exist between the transparent substrate and the film with affinity for a sample or between the film with affinity for a sample and a film without affinity for a sample.

BEST MODE FOR CARRYING OUT THE INVENTION

Hereafter, the present invention will be explained with reference to the drawings.

Figure 1A:
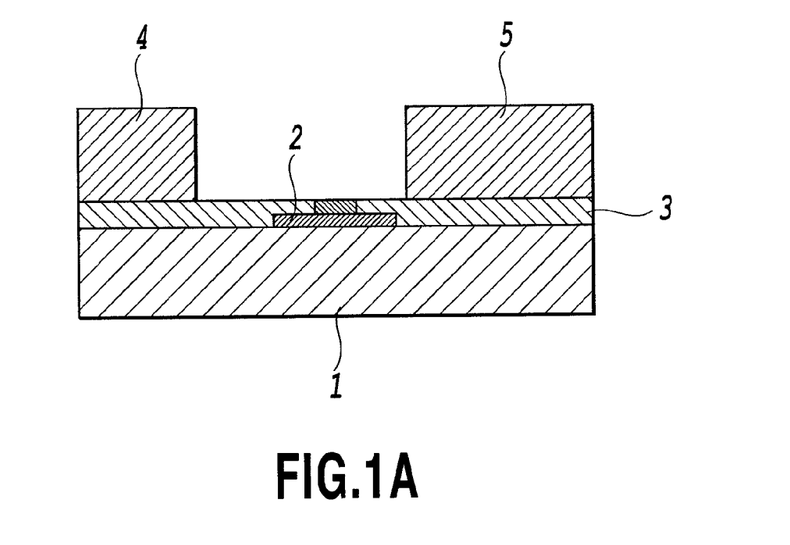
FIG. 1A is a schematic side view showing one embodiment of the sensor element of the present invention.
Figure 1B:
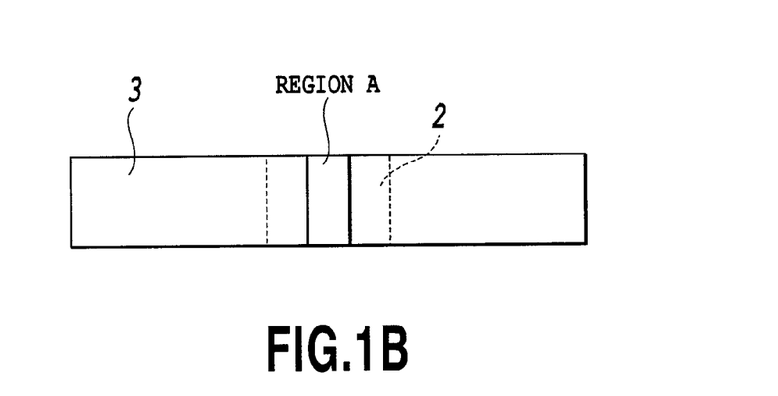
FIG. 1B is a schematic planar view showing one embodiment of the sensor element of the present invention.
Figure 2:
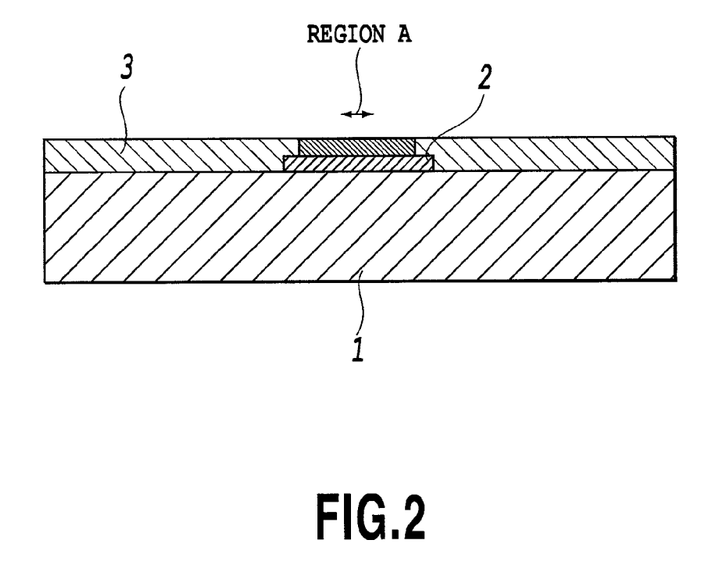
FIG. 2 is an enlarged view showing a portion including region A of a sensor element.

FIGS. 1A and 1B are simplified schematic views showing the sensor element for SPR measurement of the present invention. FIG. 1A is a side view thereof, and FIG. 1B is a planar view thereof. FIG. 2 is an enlarged view showing a portion of the element including region A. A gold thin film 2 is formed at least on a part of a substrate 1. As the substrate 1, a transparent material such as glass or transparent plastic can be used. In SPR measurement, a light needs to be made incident on an interface between the substrate and the gold thin film at an incidence angle required for SPR measurement, and any transparent material can be used so long as it can make a light incident at such an angle. However, when an SPR measurement device using a prism is used together with this sensor, the substrate preferably has the same refractive index as that of this prism.

The gold thin film 2 may cover the whole substrate 1, but does not necessarily need to cover the whole surface. It is sufficient that the gold thin film 2 covers at least a part thereof, specifically, the region in which a refractive index is measured. This gold thin film 2 can be formed by vapor-deposition, sputter-deposition, or the like.

A thin film with affinity for a sample 3 is provided on the substrate 1 having the gold thin film 2 formed on at least a part thereof. The film with affinity for a sample is not limited so long as it is made of a material that allows a sample to be impregnated in the film. When a sample is an aqueous solution, a fibrous substance or a porous film made of a cellulose material such as cellulose, nitrocellulose, or acetylcellulose or a polymer such as chitosan, polycarbonate, polystyrene, or protein can be used. Furthermore, a glass fiber or a glass porous film can be used. The film made of the above-mentioned polymer can be formed as either a fibrous substance or a porous film by suitably selecting a solvent and an casting condition.

The transparent substrate 1 on which the gold thin film 2 and the above-described thin film with affinity for a sample 3 are provided has regions A, B, and C which do not overlap each other in the surface thereof. Specifically, these regions are a measurement region (region A), a sample introduction section (region B) and a sample absorption section (region C) provided with the region A therebetween. The thin film with affinity for a sample 3 is provided on at least a part of the surface in all the regions A, B, and C, the film with affinity for a sample in the region A and the film with affinity for a sample in the region B are connected at the border of the regions A and B, and the film with affinity for a sample in the region A and the film with affinity for a sample in the region C are connected at the border of the regions A and C. Furthermore, a portion of the region A that is not covered with the thin film with affinity for a sample 3 does not have affinity for a sample. That is, exposed portions of the transparent substrate 1 and the gold thin film 2 do not have affinity for a sample. Therefore, a sample introduced into the region A enters the portion covered with the thin film with affinity for a sample. Furthermore, the surface of the film with affinity for a sample in the region A may be covered with a film without affinity for a sample. Examples of this film without affinity for a sample include metal films and solid polymer films through which a liquid cannot penetrate and films made of hydrophobic polymers when a sample is water-soluble.

The region A of the film with affinity for a sample 3 has a sample measurement section containing a molecule-recognizing film. The molecule-recognizing film is obtained by immobilizing a molecule-recognizing material on the film with affinity for a sample. As the molecule-recognizing material, one molecule of a molecule pair forming a complex can be used. As such a complex, a combination of an antigen and an antibody can be mentioned. In particular, when an antibody is used as a molecule-recognizing material, an antigen contained in a sample can be measured.

Since a refractive index in a portion within 500 nm from the gold surface is measured in the SPR method, the thickness of the film with affinity for a sample 3 in the region A is preferably 10 µm or less. When the film thickness exceeds 10 µm, the sample volume that is not measured becomes larger than necessary, and the absolute amount sensitivity is decreased.

Figure 3A:
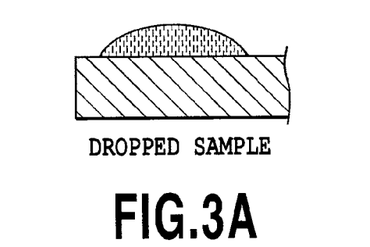
FIG. 3A shows an example of an embodiment of a sample introduction section (region B) in which nothing is provided on a film with affinity for a sample, so that a sample should be added dropwise directly onto the film with affinity for a sample.
Figure 3B:
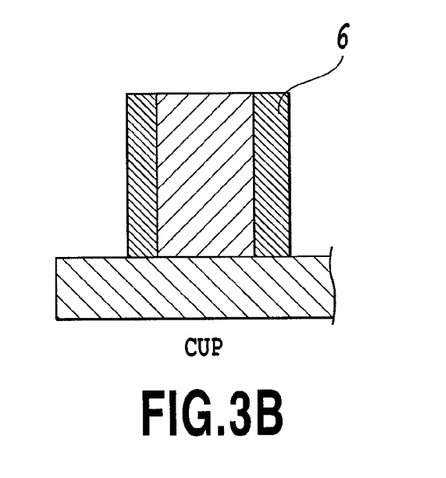
FIG. 3B shows an example of an embodiment of a sample introduction section (region B) in which a bottomless cup or tube is provided on a film with affinity for a sample to constitute a sample introduction port.
Figure 3C:
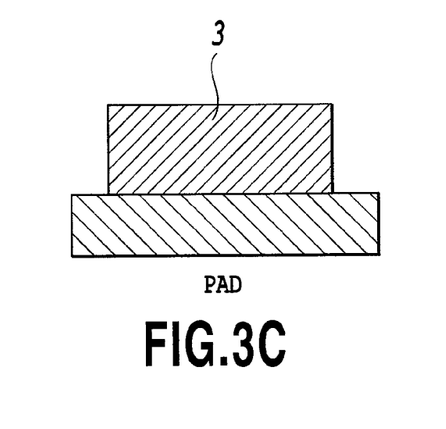
FIG. 3C shows an example of an embodiment of a sample introduction section (region B) in which a sample pad having a function of holding a liquid is provided on a film with affinity for a sample.

Furthermore, a sample introduction port is formed in the region B of the film with affinity for a sample 3. As shown in FIG. 3A, nothing may be provided on the film with affinity for a sample in the sample introduction port, so that a sample can be added dropwise directly onto the film with affinity for a sample. Furthermore, as shown in FIG. 3B, a bottomless cup or tube 6 may be provided on the film with affinity for a sample to form a sample introduction port. Furthermore, as shown in FIG. 3C, a sample pad 4 having a function of holding a liquid may be provided on a film with affinity for a sample. FIG. 3 C shows an example where a sample pad is provided as a sample introduction port. In the sample introduction port, a sample is added dropwise onto a film with affinity for a sample, into a cup or a tube, or onto the sample pad.

Furthermore, an absorption pad 5 for discharging the sample from the film with affinity for a sample is provided in the region C of the film with affinity for a sample. In a simplified structure, a film with affinity for a sample having a large volume may be used as the absorption pad 5, or a pad having a function of holding a sample liquid may be provided. As the sample pad and the pad having a function of holding a sample liquid, for example, absorption pads made of AP22 material manufactured by Millipore can be used.

In the sensor element of the present invention, a sample introduced from the introduction port flows in the film with affinity for a sample and migrates to the region C via the film with affinity for a sample in the region A. Therefore, a point in the region B, a point in the region A, and a point in the region C need to exist in one straight line on the thin film with affinity for a sample. When a sample solution is added dropwise onto the point in the region B in this straight line, the sample solution is developed (flows) along this straight line and reaches the region C via the region A.

Since the sample solution is absorbed to the absorption pad 5 in the region C and discharged from the region in this straight line, the sample is continuously supplied from the region B to the region A, and a molecule to be measured can be efficiently reacted with a molecule which forms a molecular complex together with a molecule to be measured, such as an antibody immobilized on the region A. This is an advantage particularly when a sample requires pretreatment, by which the sample volume is decreased and a small volume of the sample enters the film with affinity for a sample from the introduction port.

In measurement using this sensor element, SPR measurement is performed by making a light incident from the substrate side of this sensor element and measuring a light reflected from the gold thin film at an interface between the substrate and the gold thin film.

Furthermore, a plurality of sample measurement sections may be provided in the region A. When antibodies different from each other are immobilized on these plurality of sample measurement sections, a plurality of antigens can be detected by one SPR measurement.

In general, when a sample flows in the film with affinity for a sample, the migration speed of the solute varies depending on an interaction between a material and a structure constituting the film with affinity for a sample and the solute, and each solute reaches the region A in a different order. Since, utilizing this effect, molecules to be measured are not detected at the same time, but detected with time lags, a molecule-separating function of the immobilized molecule can be more effectively utilized, resulting in detection with high sensitivity. Furthermore, in SPR measurement, when an antigen flows closely to an antibody in the vicinity of the gold thin film, the antigen can be efficiently captured. Provision of a film without affinity for a sample has an advantage that disproportionate flow rate distributions in the direction perpendicular to the film on the opposite side of the gold thin film can be prevented in the film with affinity for a sample.

Hereafter, the examples of the present invention will be explained more specifically with reference to the drawings. The scope of the present invention is not limited to the following examples.

Example 1

Gold Chip with 4-µm Cellulose Film

A sensor element having a structure shown in FIGS. 1A and 1B was prepared by the following procedures.

1. First, a BK7 glass was used as a substrate 1, and a titanium film having a thickness of 1 nm was formed on the BK7 glass and a thin film 2 composed of a gold film having a thickness of 45 nm thereon were formed in the center of the substrate by sputtering. Titanium was used to improve adhesion of the gold thin film to the substrate. Thus, a gold thin film was formed on the region A of the sensor element.

2. A solution obtained by dissolving mixed nitrocellulose (Advantech) in a mixed solvent containing acetone as a main component and an alcohol was used to form a film with affinity for a sample made of a porous film having a thickness at the center of 4 µm on the whole surface of the glass substrate with the gold thin film by a spin coat technique.

3. Anti-human IgG (Sigma) was immobilized on the film with affinity for a sample by spotting so that the region A should be included, in which a gold thin film exists, and SPR can be detected. Furthermore, the region A portion was blocked using SuperBlock PBS (Pierce).

4. As shown in FIG. 1A, a sample pad (Millipore, AP22 material) was fixed on the film with affinity for a sample so that the pad should not overlap the portion on which the antibody was immobilized.

5. As shown in FIG. 1A, an absorption pad (Millipore, AP22 material) was set in the region C.

The glass surface of the sensor element obtained as described above was firmly attached to a prism of Handy SPR (NTT-AT), an SPR measurement device, using a refractive index matching oil. Subsequently, when cow's milk containing 10 μg/mL goat IgG was added dropwise onto the sample pad, an increase in the refractive index was observed when the liquid reached the region A, but an increase in the refractive index due to an adsorption reaction of the antigen and the antibody was not observed. On the other hand, when cow's milk containing 10 μg/mL human IgG was added dropwise onto a sensor element similarly prepared, a change in an SPR signal due to adsorption specific to human IgG was observed. It was found that immunoassay can be performed by this sensor element without preparing a pump or a special passage.

When such a sensor element prepared as in this example is stored, measurement of an antigen by an antigen-antibody reaction can be performed by setting the sensor element on an SPR device and adding dropwise a sample for each measurement, and an antigen can be detected conveniently.

Example 2

Multiple Antibodies

Figure 4A:
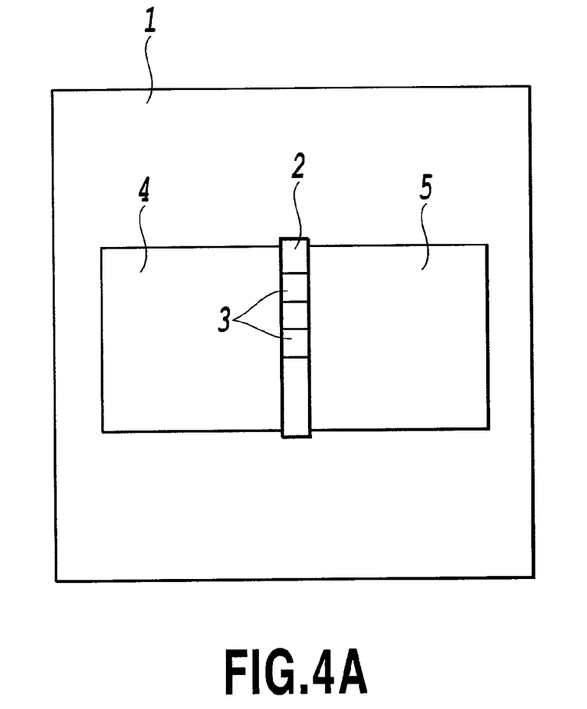
FIG. 4A is a simplified schematic side view showing another embodiment of the sensor element of the present invention.
Figure 4B:
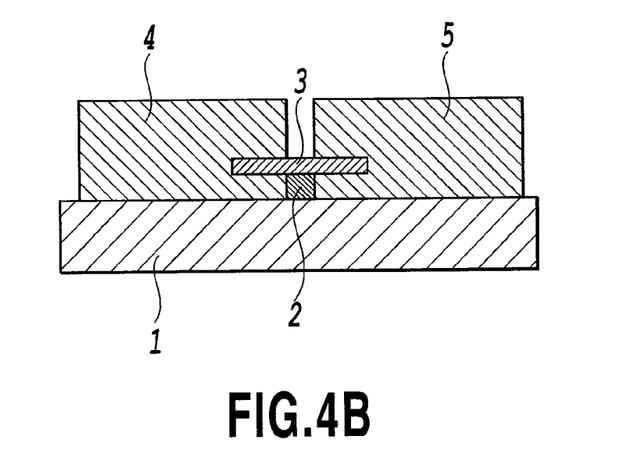
FIG. 4B is a simplified schematic planar view showing another embodiment of the sensor element of the present invention.
Figure 5A:
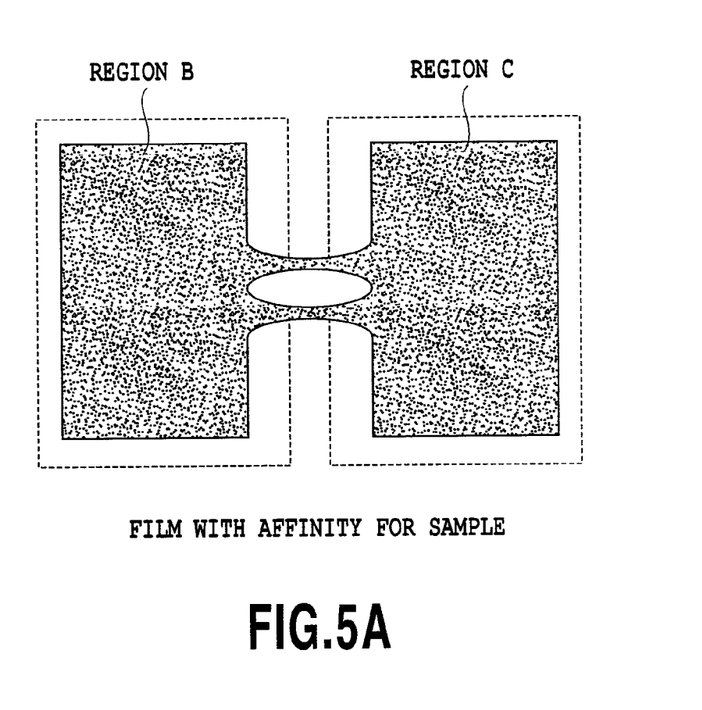
FIG. 5A shows a pattern of a film with affinity for a sample.
Figure 5B:
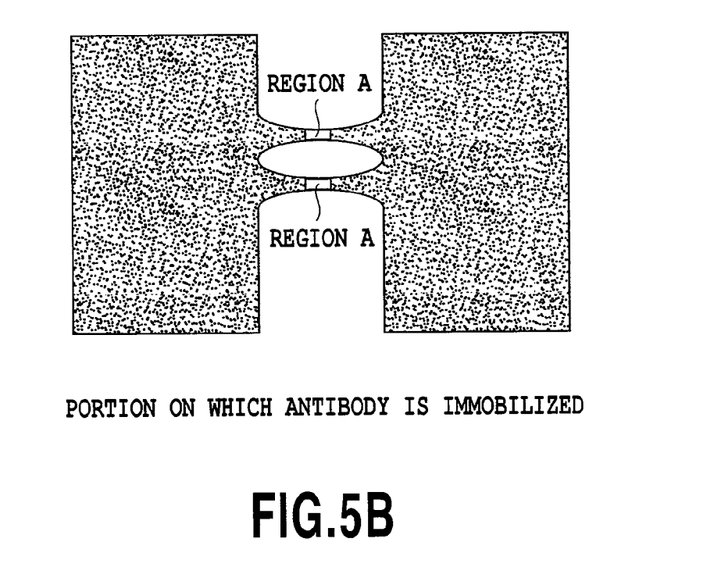
FIG. 5B shows a portion on which an antibody is immobilized.

A sensor element shown in FIGS. 4A and 4B was prepared by the same preparation procedures as in Example 1. In this element, a part of the film with affinity for a sample was removed as shown in FIG. 5A to restrict a region of the film with affinity for a sample in which the sample was allowed to flow. Two kinds of antibodies, anti-human IgG (Sigma) and anti-goat IgG (Sigma), were immobilized on the two narrowed sites.

This sensor element was firmly attached to a prism of DKK-20 (DKK), an SPR measurement device, using a refractive index matching oil.

Cow's milk containing human IgG and goat IgG was added dropwise onto the sample pad, and SPR signals thereof in the region A were recorded. When measurement was repeated with samples comprising cow's milk containing human IgG and goat IgG at different concentrations while replacing this sensor element for each measurement, SPR signals corresponding to antigens specific to the immobilized antibodies were obtained in the region A. It was confirmed that a plurality of kinds of antigens could be detected with the concentration information thereof.

INDUSTRIAL APPLICABILITY

According to the present invention, simple SPR measurement with high sensitivity can be achieved without the need of a mechanical solution-sending mechanism. Furthermore, a concentration of a specific molecule in a liquid sample can be simply and rapidly measured, and the present invention is useful for detection of a virus or for measurement or rapid diagnosis of a disease marker or an environmental pollutant.

The invention claimed is:

1. A sensor element for surface plasmon resonance (SPR) measurement utilizing an SPR effect, wherein the sensor element comprises:
   a transparent substrate;
   a gold thin film formed on at least a part of the transparent substrate; and
   a thin film with affinity for a sample provided on the transparent substrate having the gold thin film formed on at least a part thereof;
   wherein the transparent substrate having the gold thin film and the thin film with affinity for a sample provided thereon has a measurement region (region A), a sample introduction section (region B) and a sample absorption section (region C) being provided with the region A therebetween, the three regions A, B, and C being located at different portions from each other on the transparent substrate so as to not overlap each other,
   wherein the thin film with affinity for a sample is provided on at least a part of the surface in all the regions A, B, and C, the thin film with affinity for a sample in the region A is provided with a sample measurement section containing a molecule-recognizing film, an introduction port is formed on the film with affinity for a sample in the region B, and an absorption pad is provided on the film with affinity for a sample in the region C so that the whole region C is covered,
   wherein the sample measurement section comprises:
      a first portion comprising an immobilized first molecule-recognizing material, a molecule of which forms a first molecular complex with a first molecule of the sample to be measured, the first portion being located on a first narrowed region; and
      a second portion comprising an immobilized second molecule-recognizing material, a molecule of which forms a second molecular complex with a second molecule of the sample to be measured, the second portion being located on a second narrowed region separated from the first narrowed region,
   wherein a point in the region B, a point in the first portion of the sample measurement section of region A, and a point in the region C exist in a first straight line on the thin film with affinity for a sample, such that a second straight line connecting the first and second portions of the sample measurement section is substantially perpendicular to the first straight line, and
   wherein the surface of the thin film with affinity for a sample in the region A is covered with a film without affinity for a sample.

2. The sensor element for SPR measurement according to claim 1, wherein the region A is provided with a plurality of sample measurement sections.

3. The sensor element for SPR measurement according to claim 1, wherein at least one of the molecules that forms the first or second molecular complex with the first or second molecule of the sample to be measured is an antibody.

4. A sensor element for surface plasmon resonance (SPR) measurement utilizing an SPR effect, the sensor element comprising:
   a transparent substrate having a measurement region (region A) positioned between a sample introduction section (region B) and a sample absorption section (region C), the three regions A, B, and C being located at different portions from each other on the transparent substrate so as to not overlap each other;
   a gold thin film formed on at least a portion of the transparent substrate,
   a thin film with affinity for a sample positioned on at least a portion of all the regions A, B, and C of the transparent substrate, the thin film with affinity for a sample including, in the region A,
      a sample measurement section containing a molecule-recognizing film, and a point on the thin film with affinity for a sample in each of the regions A, B, and C existing in a first straight line, the sample measurement section containing a molecule-recognizing film provided with a first sample measurement section and a second sample measurement section,
      the first sample measurement section comprising an immobilized first molecule-recognizing material a molecule of which forms a first molecular complex with a first molecule of the sample to be measured, and the second sample measurement section comprising an immobilized second molecule-recognizing material a molecule of which forms a second molecular complex with a second molecule of the sample to be measured, the first and second sample measurement sections being located on a first narrowed region and a second narrowed region separated from the first narrowed region, respectively, between region B and region C, wherein when the first sample measurement section is arranged on the first straight line, a second straight line connecting the first and the second sample measurement sections is substantially perpendicular to the first straight line;

an introduction port formed on the thin film with affinity for a sample in the region B;

an absorption pad positioned on the thin film with affinity for a sample in the region C; and a film without affinity for a sample positioned so as to cover the thin film with affinity for a sample in the region A.

5. The sensor element according to claim 4, wherein the thin film with affinity for a sample includes, in region A, a plurality of sample measurement sections.

6. The sensor element according to claim 4, wherein at least one of the molecules which form the first molecular complex with the first molecule of the sample and the second molecular complex with the second molecule of the sample is an antibody.

7. The sensor element according to claim 1, wherein the thin film without affinity for a sample comprises a film through which a liquid cannot penetrate.

8. The sensor element according to claim 7, wherein the thin film without affinity for a sample is positioned directly on the surface of the thin film with affinity for a sample in the region A.

9. The sensor element according to claim 7, wherein the thin film without affinity for a sample comprises a metal film or a solid polymer film.

10. The sensor element according to claim 1, wherein the points that exist in a first straight line on the thin film with affinity for a sample in each of the regions A, B, and C are separate and distinct from each other such that a sample introduced to the sensor element at the introduction port moves along the first straight line on the thin film with affinity for a sample as the sample flows from region B to region C through region A.

11. The sensor element according to claim 1, wherein regions B and C of the transparent substrate are positioned on diametrically opposing sides of region A of the substrate.

12. The sensor element according to claim 4, wherein the thin film without affinity for a sample comprises a film through which a liquid cannot penetrate.

13. The sensor element according to claim 12, wherein the thin film without affinity for a sample is positioned directly on the surface of the thin film with affinity for a sample in the region A.

14. The sensor element according to claim 12, wherein the thin film without affinity for a sample comprises a metal film or a solid polymer film.

15. The sensor element according to claim 4, wherein the points that exist in a first straight line on the thin film with affinity for a sample in each of the regions A, B, and C are separate and distinct from each other such that a sample introduced to the sensor element at the introduction port moves along the first straight line on the thin film with affinity for a sample as the sample flows from region B to region C through region A.

16. The sensor element according to claim 4, wherein regions B and C of the transparent substrate are positioned on diametrically opposing sides of region A of the substrate.

* * * * *